United States Patent [19]

Sato et al.

[11] Patent Number: 5,306,839
[45] Date of Patent: Apr. 26, 1994

[54] PHOSPHITE COMPOUNDS

[75] Inventors: Keiichi Sato; Masaki Takai, both of Tokyo; Yuji Kawaragi, Yokohama; Tooru Ookoshi, Machida, all of Japan

[73] Assignee: Mitsubishi Kasei Corporation, Tokyo, Japan

[21] Appl. No.: 25,255

[22] Filed: Mar. 2, 1993

Related U.S. Application Data

[62] Division of Ser. No. 850,267, Mar. 12, 1992.

[30] Foreign Application Priority Data

Mar. 14, 1991 [JP] Japan .................................. 3-049862

[51] Int. Cl.$^5$ ................................................ C07F 9/02
[52] U.S. Cl. .......................................................... 558/70
[58] Field of Search ................. 568/460, 465; 546/250; 524/101; 558/70, 113; 258/89

[56] References Cited

PUBLICATIONS

Sarceno "Chemical Abstract" vol. 67(18) 83690g 1967.
Niedzieski et al "Chemical Abstract" vol. 69(3):10216p 1968.
Kuliev et al "Chemical Abstracts", vol. 67(7):28558z (1967).
Chasar "Chemical Abstracts", vol. 100(13):102927h (1984).
Chasar "Chemical Abstracts" vol. 103(14) 105787k (1985).

*Primary Examiner*—Werren B. Lone
*Attorney, Agent, or Firm*—Oblon, Spivak, McClelland, Maier & Neustadt

[57] ABSTRACT

A method for producing an aldehyde, which comprises reacting an olefinic compound with carbon monoxide and hydrogen in the presence of a Group VIII metal compound and an organic phosphite compound to produce a corresponding aldehyde, wherein an organic phosphite compound of the formula (I):

$$P(OR_1)(OR_2)(OR_3) \qquad (I)$$

wherein each of $R_1$ and $R_2$ which may be the same or different, is a 2-naphthyl group which may have a substituent, provided that at least one of $R_1$ and $R_2$ is a substituted 2-naphthyl group of the formula (II):

(II)

[structure of substituted naphthalene with $R_5$, $R_6$, $R_7$, $R_8$, $R_9$, $R_4$]

wherein $R_4$ is a $C_{1-30}$ organic group, and each of $R_5$, $R_6$, $R_7$, $R_8$ and $R_9$ which may be the same or different, is a hydrogen atom or an organic group, and $R_3$ is ① a 2-naphthyl group which may have a substituent, ② a phenyl group which may have a substituent, or ③ an alkyl group which may have a substituent, is used as said organic phosphite compound.

10 Claims, No Drawings

PHOSPHITE COMPOUNDS this is a division of application Ser. No. 07/850,267, filed on Mar. 12, 1992.

The present invention relates to a method for producing an aldehyde, which comprises reacting an olefinic compound with carbon monoxide and hydrogen. Aldehydes obtainable by the present invention are compounds useful as starting materials for plasticizers for resins such as a vinyl chloride resin. The present invention also relates to novel phosphite compounds.

For producing an aldehyde by reacting an olefinic compound with carbon monoxide and hydrogen, it is known to those skilled in the art to employ a hydroformylation catalyst having a Group VIII metal such as rhodium modified by a phosphorus-containing ligand. It is also known that the catalytic activities are substantially influenced by the type of the phosphorus-containing compound used as the ligand even under the same reaction conditions. On the other hand, it is known that the reactivity of the hydroformylation reaction is substantially affected by the structure of the olefinic compound as the substrate, and a di- or more-substituted i.e. poly-substituted olefin such as a branched terminal olefin, a linear internal olefin or a branched internal olefin (hereinafter generally referred as "poly-substituted olefin") is inferior in the reactivity to a linear terminal olefin. As a method for improving the hydroformylation reaction rate of such a poly-substituted olefin with low reactivity, Japanese Unexamined Patent Publication No. 123134/1982 discloses a hydroformylation method for a branched olefin such as 2-methyl-1-hexene wherein a rhodium catalyst modified with a phosphite ligand such as tris(2-t-butylphenyl)phosphite, is employed.

Further, Japanese Unexamined Patent Publication No. 123143/1987 discloses that by using a cycloalkylphosphine such as tricyclohexylphosphine, a high hydroformylation activity can be obtained even for a poly-substituted olefin such as 2-butene.

However, for producing an aldehyde industrially advantageously from such an olefinic compound with low reactivity, such conventional methods do not provide a fully satisfactory hydroformylation reaction rate, and it has been desired to develop a catalyst system having higher activities.

The present inventors have conducted an extensive research for a method for producing an aldehyde industrially advantageously by reacting an olefinic compound with carbon monoxide and hydrogen. As a result, it has been found that a desired aldehyde can be prepared at a high reaction rate by conducting the hydroformylation reaction in the presence of an organic phosphite compound having a certain specific structure in combination with a Group VIII metal compound. The present invention has been accomplished on the basis of this discovery.

Thus, the present invention provides a method for producing an aldehyde, which comprises reacting an olefinic compound with carbon monoxide and hydrogen in the presence of a Group VIII metal compound and an organic phosphite compound to produce a corresponding aldehyde, wherein an organic phosphite compound of the formula (I):

$$P(OR_1)(OR_2)(OR_3) \tag{I}$$

wherein each of $R_1$ and $R_2$ which may be the same or different, is a 2-naphthyl group which may have a substituent, provided that at least one of $R_1$ and $R_2$ is a substituted 2-naphthyl group of the formula (II):

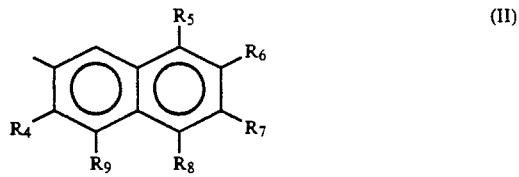

wherein $R_4$ is a $C_{1-30}$ organic group, and each of $R_5$, $R_6$, $R_7$, $R_8$ and $R_9$ which may be the same or different, is a hydrogen atom or an organic group, and $R_3$ is ① a 2-naphthyl group which may have a substituent, ② a phenyl group which may have a substituent, or ③ an alkyl group which may have a substituent, is used as said organic phosphite compound.

The present invention also provides a novel phosphite compound of the formula (III):

$$P(OR_{10})(OR_{11})(OR_{12}) \tag{III}$$

wherein each of $R_{10}$ and $R_{11}$ is a 2-naphthyl group in which at least the 3-, 6- and 8-positions are substituted by the same or different hydrocarbon groups and which may further have substituents, and $R_{12}$ is an alkyl group, or a phenyl group which may have a substituent only at the m-position and/or p-position.

Now, the present invention will be described in detail with reference to the preferred embodiments.

With respect to the olefinic compound used in the method for producing an aldehyde according to the present invention, there is no particular restriction as to its structure, so long as it is a compound having at least one olefinic double bond in its molecule. Namely, the method of the present invention can be applied to any olefinic compound such as an olefinic compound substituted only by a saturated hydrocarbon group, an olefinic compound substituted by a hydrocarbon group including an unsaturated hydrocarbon group, or an olefinic compound substituted by a functional group containing a hetero atom.

The olefinic compound substituted only by a saturated hydrocarbon group, includes, for example, a linear terminal olefinic hydrocarbon such as 1-hexene, 1-octene or 1-decene, a branched terminal olefinic hydrocarbon such as isobutene or 2-methyl-1 butene, a linear internal olefinic hydrocarbon such as cis- or trans-2-butene, cis- or trans-2-hexene, cis- or trans-3-hexene, cis- or trans-2-octene, or cis- or trans-3-octene, a branched internal olefinic hydrocarbon such as 2,3-dimethyl-2-butene, 2-methyl-2-butene, or 2-methyl-2-pentene, a terminal olefinic hydrocarbon-internal olefinic hydrocarbon mixture such as a mixture of olefin oligomer isomers like dimers to tetramers of lower olefins such as octene obtainable by dimerization of butenes or nonene obtainable by trimerization of propylene, and an alicyclic olefinic hydrocarbon such as cyclopentene, cyclohexene, 1-methylcyclohexene, cyclooctene or limonene.

The olefinic compound substituted by a hydrocarbon group including an unsaturated hydrocarbon group, includes, for example, an olefinic compound having an aromatic substituent such as styrene, α-methylstyrene or allylbenzene, and a diene compound such as 1,5-pentadiene, 1,7-octadiene or norbornadiene.

The olefinic compound substituted by a functional group containing a hetero atom, includes, for example, allyl alcohol, 3-methyl-3-buten-1-ol, 1-hydroxy-2,7-octadiene, acrylonitrile, an acrylate and a methacrylate.

Among these, the hydroformylation catalyst of the present invention is particularly effective for branched olefins for which no adequate reaction rates have been obtained by conventional catalysts because of their low reactivity, such as isobutene, 2-methyl-1-butene, 2-methyl-2-butene, 2,3-dimethyl-2-butene, an octene mixture containing various isomers obtained by dimerization of butenes, a mixture of olefin oligomer isomers such as dimers to tetramers of lower olefins, such as nonene obtained by trimerization of propylene. Among them, it is particularly effective for a $C_{4-20}$ branched internal olefinic compound. Namely, the method of the present invention is effective even for a substrate, for which no adequate catalytic activities are obtainable even by using a tricycloalkylphosphine ligand as disclosed in Japanese Unexamined Patent Publication No. 123143/1987.

In the method for producing an aldehyde according to the present invention, an organic phosphite compound of the formula (I):

wherein each of $R_1$ and $R_2$ which may be the same or different, is a 2-naphthyl group which may have a substituent, provided that at least one of $R_1$ and $R_2$ is a substituted 2-naphthyl group of the formula (II):

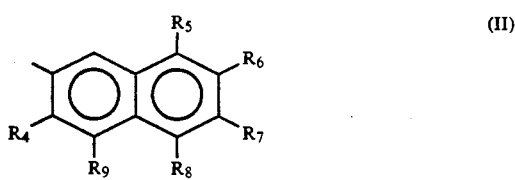

wherein $R_4$ is a $C_{1-30}$ organic group, and each of $R_5$, $R_6$, $R_7$, $R_8$ and $R_9$ which may be the same or different, is a hydrogen atom or an organic group, and $R_3$ is ① a 2-naphthyl group which may have a substituent, ② a phenyl group which may have a substituent, or ③ an alkyl group which may have a substituent, is used as said organic phosphite compound.

In the 2-naphthyl group of the formula (II) for $R_1$ and $R_2$, $R_4$ is preferably $-C(R_{13})(R_{14})R_{15}$ or an aryl group which may have a substituent, wherein each of $R_{13}$, $R_{14}$ and $R_{15}$ is a hydrogen atom, a fluorinated hydrocarbon group or a hydrocarbon group. When each of $R_{13}$, $R_{14}$ and $R_{15}$ is a hydrocarbon group, it is preferably a $C_{1-10}$ hydrocarbon group. When $R_4$ is an aryl group which may have a substituent, the substituent may be any optional organic group, so long as it does not impair the hydroformylation reaction.

When $R_4$ is $-C(R_{13})(R_{14})R_{15}$, $R_4$ is preferably bulky as a whole. Usually, as $R_4$, a branched alkyl group, preferably a $C_{3-20}$ branched alkyl group, is employed. Specifically, an i-propyl group, a s-butyl group, a t-butyl group, a s-amyl group, a t-amyl group, a t-hexyl group, a cyclohexyl group or a 1-methylcyclohexyl group may, for example, be used.

When each of $R_5$, $R_6$, $R_7$, $R_8$ and $R_9$ is an organic group, it may be any optional organic group so long as it does not impair the hydroformylation reaction.

Such an organic group, or an organic group as the substituent in the case where $R_4$ is an aryl group which may have a substituent, may, for example, be a $C_{1-20}$ alkyl group such as a methyl group, an ethyl group, a n-propyl group, an i-propyl group, a n-butyl group, a s-butyl group, an i-butyl group, a t-butyl group, a n-amyl group, a t-amyl group, a n-hexyl group, a cyclopentyl group, a cyclohexyl group, an octyl group, a nonyl group, a decyl group or an octadecyl group, a $C_{6-30}$ aryl group such as a phenyl group, a tolyl group, a xylyl group, a p-biphenyl group or a naphthyl group, a $C_{7-30}$ aralkyl group such as a benzyl group, a functional group having a hetero atom, such as a halogen, an alkoxy group, a carboalkoxy group or an alkylamino group, for example, the substituent containing a halogen atom as a functional group may be a halogen such as fluorine, chlorine or bromine, or a fluorinated alkyl group such as a trifluoromethyl group, a pentafluoroethyl group or a heptafluoropropyl group, the substituent containing an alkoxy group as a functional group, may be a methoxy group, an ethoxy group, a n-propoxy group or an i-propoxy group, the substituent containing a carboalkoxy group as a functional group, may be an acetyl group, a propionyl group, a benzoyl group, a carbomethoxy group, and the substituent containing an alkylamino group as a functional group, may be a dimethylamino group or a diethylamino group.

Either one of substituents $R_1$ and $R_2$ has a structure of the formula (II), and the other may have the same structure or a different structure. As a 2-naphthyl group having a substituent of a different structure, a group of the formula (IV):

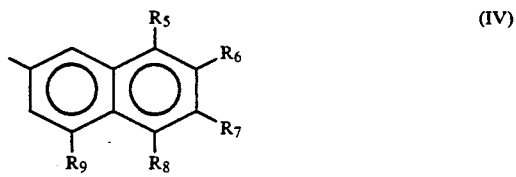

wherein $R_5$, $R_6$, $R_7$, $R_8$ and $R_9$ are as defined in the formula (II), may be mentioned.

The organic group for $R_5$, $R_6$, $R_7$, $R_8$ and $R_9$ may, for example, be a $C_{1-20}$ alkyl group such as a methyl group, an ethyl group, a n propyl group, an i-propyl group, a n-butyl group, a s-butyl group, an i-butyl group, a t-butyl group, a n-amyl group, a t-amyl group, a n-hexyl group, a cyclopentyl group, a cyclohexyl group, an octyl group, a nonyl group, a decyl group or an octadecyl group, a $C_{6-30}$ aryl group such as a phenyl group, a tolyl group, a xylyl group, a p-biphenyl group or a naphthyl group, a $C_{7-30}$ aralkyl group such as a benzyl group, or a functional group having a hetero atom, such as a halogen, an alkoxy group, a carboalkoxy group or an alkylamino group, for example, the substituent containing a halogen atom as a functional group may be a halogen such as fluorine, chlorine or bromine, or a fluorinated alkyl group such as a trifluoromethyl group, a pentafluoroethyl group or a heptafluoropropyl group, the substituent containing an alkoxy group as a functional group may be a methoxy group, an ethoxy group, a n-propoxy group or an i-propoxy group, the substituent containing a carboalkoxy group as a functional group may be an acetyl group, a propionyl group, a benzoyl group or a carbomethoxy group, and the substituent containing an alkylamino group as a functional group may be a dimethylamino group or a diethylamino group.

When $R_3$ is a 2-naphthyl group which may have a substituent, it is preferably a 2-naphthyl group of the formula (II) or (IV). It is particularly preferred to employ the one having a 2-naphthyl group of the formula (II).

Specific examples include a phosphite compound of the formula (I) wherein each of $R_1$, $R_2$ and $R_3$ is a 2-naphthyl group of the formula (II), such as tris(3-isopropyl-2-naphthyl)phosphite, tris(3,6-diisopropyl 2-naphthyl)phosphite, tris(3-tert-butyl-2-naphthyl)phosphite, tris(3,6-ditert-butyl-2-naphthyl)phosphite, tris(3-tert-amyl-2 -naphthyl)phosphite, tris(3,6-ditert-amyl-2-naphthyl)phosphite, tris[3-(1,1,2-trimethylpropyl)-2-naphthyl]phosphite, tris[3,6-di(1,1,2-trimethylpropyl)-2-butyl]phosphite, tris(3-phenyl-2-naphthyl)phosphite, tris(3,6-diphenyl-2-naphthyl)phosphite, tris(3-cyclohexyl-2-naphthyl)phosphite, tris(3,6-dicyclohexyl-2-naphthyl)phosphite, tris(3 tert-butyl 6-methoxy-2-naphthyl)phosphite, tris(3,6-ditert-butyl-7-methoxy-2-naphthyl)phosphite, tris(3,6,8-trimethyl-2-naphthyl)phosphite, bis(3,6-ditert-butyl-2 naphthyl)(3-tert-butyl-2-naphthyl)phosphite, bis(3,6-ditert-butyl-2-naphthyl)(3,6-ditert-amyl-2-naphthyl)phosphite, bis(3,6-ditert-butyl-2-naphthyl)(3,6-diemthyl-2-naphthyl)phosphite or bis(3,6 ditert-butyl-2-naphthyl)(3,6,8-trimethyl 2-naphthyl)-phosphite; a phosphite compound of the formula (I) wherein each of $R_1$ and $R_2$ is a 2-naphthyl group of the formula (II) and $R_3$ is a 2-naphthyl group of the formula (IV), such as bis(3,6-dimethyl-2-naphthyl)(2-naphthyl)phosphite, bis(3,6-diisopropyl-2-naphthyl)(2 naphthyl)phosphite, bis(3,6-ditert-butyl-2-naphthyl)(2 naphthyl)phosphite, bis(3,6-ditert-amyl-2-naphthyl)(2-naphthyl)phosphite, bis(3,6-diphenyl-2-naphthyl)(2 naphthyl)phosphite, bis(3,6-ditert-butyl-2 naphthyl)(6-tert-butyl-2-naphthyl)phosphite, bis(3,6-ditert-butyl-2-naphthyl)(6,7-dimethyl-2-naphthyl)phosphite, bis(3,6,8-tritert-butyl-2-naphthyl)(2-naphthyl)phosphite, bis(3,6,8-tritert-butyl- 2-naphthyl)(6-tert-butyl-2-naphthyl)-phosphite or bis(3,6,8-trimethyl-2-naphthyl)(2-naphthyl)phosphite; and a phosphite compound of the formula (I) wherein $R_1$ is a 2-naphthyl group of the formula (II) and each of $R_2$ and $R_3$ is a naphthyl group of the formula (IV), such as (3,6-diisopropyl-2-naphthyl)-bis(2 naphthyl)phosphite, (3,6-ditert-butyl-2-naphthyl)-bis(2-naphthyl)phosphite, (3,6-ditert-amyl-2-naphthyl}bis(2-naphthyl)phosphite, 3,6-ditert-butyl-2-naphthyl)(6-tert-butyl-2-naphthyl)(2-naphthyl)phosphite or (3,6,8-tritert-butyl-2-naphthyl)bis(2-naphthyl)phosphite. Among them, a phosphite compound of the formula (I) wherein each of $R_1$, $R_2$ and $R_3$ is a 2-naphthyl group of the formula (II), such as tris(3,6-ditert-butyl-2-naphthyl)phosphite or tris(3,6-ditert-amyl-2-naphthyl)-phosphite is preferred.

The substituent in a case where $R_3$ is a phenyl group which may have a substituent, may be any optional organic group so long as it does not impair the hydroformylation reaction. For example, it may be a $C_{1-30}$ hydrocarbon group such as an alkyl group, an aryl group or an aralkyl group, a substituent containing a halogen atom as a functional group, a substituent containing an oxygen atom as a functional group, such as an alkoxy group or a carbonyl group, a substituent containing a nitrogen atom as a functional group, such as an amino group or a nitro group, or a substituent containing a sulfur as a functional group, such as a sulfonyl group.

The hydrocarbon group may be a $C_{1-20}$ alkyl group such as a methyl group, an ethyl group, a n-propyl group, an i-propyl group, a n-butyl group, a s-butyl group, an i-butyl group, a t-butyl group, a n-amyl group, a t-amyl group, a n-hexyl group, a cyclopentyl group, a cyclohexyl group, an octyl group, a nonyl group, a decyl group or an octadecyl group; a $C_{6-30}$ aryl group such as a phenyl group, a tolyl group, a xylyl group, a p-biphenyl group or a naphthyl group; or a $C_{7-30}$ aralkyl group such as a benzyl group. The substituent containing a halogen atom as a functional group, may, for example, be a halogen such as fluorine, chlorine or bromine, or a fluorinated alkyl group such as a trifluoromethyl group, a pentafluoroethyl group or a heptafluoropropyl group. The substituent containing an oxygen atom as a functional group, may, for example, be an alkoxy group such as a methoxy group, an ethoxy group, a n-propoxy group or an i-propoxy group, or a substituent containing a carbonyl group, such as an acetyl group, a propionyl group, a benzoyl group, a carbomethoxy group or a carboethoxy group, or a cyclic substituent containing an oxygen, such as a furyl group or a pyranyl group. The substituent containing a nitrogen atom as a functional group, may, for example, be a substituent containing a nitrogen atom, such as an amino group, a dimethylamino group, a diethylamino group, an aminoethyl group, a cyano group, a cyanoethyl group or a nitro group. The substituent containing a sulfur atom as a functional group, may, for example, be a substituent containing a sulfonyl group such as a methane sulfonyl group, a benzene sulfonyl group or a toluene sulfonyl group.

The position of the substituent may be the o-, m- or p-position. The number of such substituents is not particularly limited and may be from one to five.

Specific examples include a phosphite compound of the formula (I) wherein each of $R_1$ and $R_2$ is a 2-naphthyl group of the formula (II) which has hydrocarbon groups at the 3-, 6- and 8-positions, and $R_3$ is a phenyl group which may have a substituent only at the m-position and/or p-position, such as bis(3,6,8-triisopropyl-2-naphthyl)phenylphosphite, bis(3,6,8-tri-s-butyl-2-naphthyl)phenylphosphite, bis(3,6,8-tri-s-butyl-2-naphthyl)(p-biphenyl)phosphite, bis(3,6,8-tritert-butyl-2-naphthyl)phenylphosphite, bis(3,6,8 tritert-amyl-2-naphthyl)phenylphosphite, bis(3,6,8-triphenyl-2-naphthyl)phenylphosphite, bis(3,6,8-tritert-amyl-2-naphthyl(p-biphenyl)phosphite, )bis(3,6,8-tritert-butyl-2-naphthyl)(p-tolyl)phosphite, bis(3,6,8 tritert butyl-2-naphthyl)(m tolyl)phosphite, bis(3,6,8-tritert-butyl-2-naphthyl)(3,4-dimethylphenyl)phosphite, bis(3,6,8-tritert-butyl-2-naphthyl)(3,4,5-trimethylphenyl)phosphite, bis(3,6,8-tritert-butyl-2-naphthyl)(p-tert-butylphenyl)phosphite, bis(3,6,8-tritert-butyl-2-naphthyl)(m-tert-butylphenyl)phosphite, bis(3,6,8-tritert-butyl-2-naphthyl)(p-biphenyl)phosphite, bis(3,6,8-tritert-butyl-2-naphthyl)(p-fluorophenyl)phosphite, bis(3,6,8-tritert-butyl-2-naphthyl)(p-trifluoromethylphenyl)phosphite, bis (3,6,8-tritert-butyl-2-naphthyl)(p-acetylphenyl)-phosphite, bis(3,6,8-tritert-butyl-2-naphthyl)(p-benzoylphenyl)phosphite, bis(3,6,8 tritert-butyl-2-naphthyl)(p-methoxyphenyl)phosphite, bis(3,6,8-tritertbutyl-2-naphthyl)(p-carbomethoxyphenyl)phosphite, bis(3,6,8-tritert-butyl 2 naphthyl)(p-dimethylaminophenyl)-phosphite, bis(3,6,8-tritert-butyl-2-naphthyl)(p-methanesulfonylphenyl)phosphite or bis(3,6,8-tritertbutyl-2-naphthyl)(p-toluenesulfonylphenyl)phosphite; a phosphite compound of the formula (I) wherein each of $R_1$ and $R_2$ is a 2-naphthyl group of the formula (II) and $R_3$ is a phenyl group which may have a substituent only at the m-position and/or p-position, such as bis(3,6-diisopropyl-2-naphthyl)phenylphosphite, bis(3,6-ditert-butyl 2-naphthyl)phenylphosphite, bis(3,6-ditert-amyl-2-naphthyl)phenylphosphite, bis(3,6-diphenyl-2-naphthyl)phenylphosphite, bis(3,6-ditert-butyl 2-naphthyl)(p tolyl)phosphite, bis(3,6-ditert-butyl-2-naphthyl)(m-tolyl)phosphite, bis(3,6-ditert-butyl-2-naphthyl)(p-tert-butylphenyl)phosphite, bis(3,6 ditertbutyl-2-naphthyl)(m-tert-butylphenyl)phosphite, bis(3,6-ditert-butyl-2-naphthyl)(p-biphenyl)phosphite, bis(3,6 -di-s-butyl-2-naphthyl)phenylphosphite, bis(3,6-ditertbutyl-2-naphthyl)(p-fluorophenyl)phosphite, bis(3,6-ditert-butyl-2-naphthyl)(p-trifluoromethylphenyl)phosphite, bis(3,6-ditert-butyl-2-naphthyl)(p-acetylphenyl)phosphite, bis(3,6-ditert-butyl-2-naphthyl)(p-benzoylphenyl)-phosphite, bis(3,6-ditertbutyl-2-naphthyl)(p-methoxyphenyl)phosphite, bis(3,6-ditert-butyl-2-naphthyl)(p-carbomethoxyphenyl)phosphite, bis(3,6-ditert-butyl-2-naphthyl)(p-dimethylaminophenyl)phosphite, bis(3,6-ditert-butyl-2-naphthyl)(p-methanesulfonylphenyl)-phosphite, bis(3,6-ditert-butyl-2-naphthyl)(p-toluenesulfonylphenyl)phosphite, (3,6-ditert butyl-2-naphthyl)(3,6,8-tritert-butyl-2-naphthyl)phenylphosphite, or (3,6 ditert-butyl-2-naphthyl)(3,6,8-tritert-butyl-2-naphthyl)(p-tolyl)phosphite; a phosphite compound of the formula (I) wherein each of $R_1$ and $R_2$ is a 2-naphthyl group of the formula (II) and $R_3$ is a phenyl group which has a substituent at the o-position, such as bis(3,6-ditert-butyl-2-naphthyl)(o-tolyl)phosphite, bis(3,6-ditert-butyl 2-naphthyl)(o-isopropylphenyl)phosphite, bis(3,6-ditert-butyl-2-naphthyl)(o-tertbutylphenyl)-phosphite, bis(3,6-ditert-butyl-2-naphthyl)(2,4-ditertbutylphenyl)phosphite, bis(3,6-ditert-butyl-2-naphthyl)(2-tert-butyl-4-methylphenyl)phosphite, bis(3,6-ditert-butyl-2-naphthyl)(2-tert-butyl-4 -phenylphenyl)-phosphite, bis(3,6-ditert-butyl-2-naphthyl)(2-tert-butyl-4-methoxyphenyl)phosphite, bis(3,6-ditert-butyl-2-naphthyl)(2-tert-butyl-4-acetylphenyl)phosphite, bis(3,6-ditert-butyl-2-naphthyl)(2-tert-butyl-4-benzoylphenyl)phosphite, bis(3,6-ditert-butyl-2-naphthyl}(2-tert-butyl-4-benzenesulfonylphenyl)phosphite, bis(3,6-ditert-amyl-2-naphthyl)(o-tolyl)phosphite or bis(3,6-diphenyl-2-naphthyl)(o-tolyl)phosphite; and a phosphite compound of the formula (I) wherein $R_1$ is a 2-naphthyl group of the formula (II), and $R_2$ is a 2-naphthyl group of the formula (IV), such as (3,6,8-tritert-butyl-2-naphthyl)(2-naphthyl)phenylphosphite, (3,6,8-tritert-butyl-2-naphthyl)(2-naphthyl)(p-tolyl)phosphite, (3,6,8-tritert-butyl-2-naphthyl)(2-naphthyl)(m-tolyl)-phosphite, (3,6,8-tritert-butyl-2 naphthyl)(2-naphthyl)-(o-tolyl)phosphite, (3,6,8-tritert-butyl-2-naphthyl)(2-naphthyl)(p-tertbutylphenyl)phosphite, (3,6,8-tritert-butyl-2-naphthyl)(2-naphthyl)(o-tert-butylphenyl)-phosphite, (3,6,8-tritert-butyl-2-naphthyl)(2-naphthyl)(2,4-ditertbutylphenyl)phosphite, (3,6,8-tritert-butyl-2-naphthyl)(2-naphthyl)(p-biphenyl)phosphite, (3,6,8-triphenyl-2-naphthyl)(2-naphthyl)phenylphosphite, (3,6-ditert-butyl-2-naphthyl)(2-naphthyl)phenylphosphite, (3,6-ditert-butyl-2-naphthyl)(2-naphthyl)(p-tolyl)phosphite, (3,6-ditert-butyl-2-naphthyl)(2-naphthyl)(o-tolyl)phosphite, (3,6-ditert-butyl-2 -naphthyl)(2-naphthyl)(o-tert-butylphenyl)phosphite, (3,6-ditert-butyl-2-naphthyl)(2-naphthyl)(2,4-ditertbutylphenyl)- phosphite or (3,6-ditert-butyl-2-naphthyl)(2-naphthyl)(p-biphenyl)phosphite.

When $R_3$ is an alkyl group which may have a substituent, it is preferably a $C_{1-20}$ linear, branched or cyclic alkyl group. The linear alkyl group may, for example, be a methyl group, an ethyl group, a n-propyl group, a n-butyl group, a n-amyl group, a n-hexyl group, an octyl group, a nonyl group, a decyl group or an octadecyl group. The branched alkyl group may, for example, be an i-propyl group, a s-butyl group, an i-butyl group, a t-butyl group, a t-amyl group or a t-hexyl group. The cyclic alkyl group may, for example, be a cyclopentyl group, a cyclohexyl group, a 2-methylcyclohexyl group, a 2,2-dimethylcyclohexyl group, a 2,4-dimethylcyclohexyl group or a 2-norbornyl group. Among them, a branched or cyclic alkyl group such as a t-butyl group, a t-amyl group or a cyclohexyl group, is preferred.

Specific examples include bis(3,6-ditert-butyl-2-naphthyl)methylphosphite, bis(3,6,8-tritert butyl-2-naphthyl)methylphosphite, bis(3,6-ditert-butyl-2-naphthyl)ethylphosphite, bis(3,6,8-tritert-butyl-2-naphthyl)ethylphosphite, bis(3,6-ditert-butyl-2-naphthyl)tert-butylphosphite, bis(3,6,8-tritert-butyl-2-naphthyl)tert-butylphosphite, bis(3,6-ditert-butyl-2 -naphthyl)tert-amylphosphite, bis(3,6,8-tritert-butyl-2-naphthyl)tert-amylphosphite, bis(3,6-diisopropyl-2-naphthyl)cyclohexylphosphite, bis(3,6-ditert-butyl-2-naphthyl)cyclohexylphosphite, bis(3,6-ditert-amyl-2-naphthyl)cyclohexylphosphite, bis(3,6-diphenyl-2-naphthyl)cyclohexylphosphite, bis(3,6,8-tritert-butyl-2-naphthyl)cyclohexylphosphite, bis(3,6,8-tritert-amyl-2-naphthyl)cyclohexylphosphite, bis(3,6,8-tritert-amyl-2-naphthyl)2-methylcyclohexylphosphite, (3,6-ditert-butyl-2-naphthyl)(3,6,8-tritert-butyl-2-naphthyl)cyclohexylphosphite, (3,6,8-tritert-butyl-2-naphthyl)(2-naphthyl)cyclohexylphosphite, and (3,6,8-tritert-amyl-2-naphthyl)(2 naphthyl)cyclohexylphosphite.

Especially, a novel phosphite compound of the formula (I) wherein each of $R_1$ and $R_2$ is a 2-naphthyl group having hydrocarbon groups at the 3-, 6- and 8-positions and $R_3$ is a phenyl group which may have a substituent only at the m-position and/or p-position, or an alkyl group, i.e. a novel phosphite compound of the formula (III):

$$P(OR_{10})(OR_{11})(OR_{12}) \qquad (III)$$

wherein each of $R_{10}$ and $R_{11}$ is a 2-naphthyl group which is substituted by the same or different hydrocarbon groups at least at the 3-, 6- and 8-positions and which may have other substituents, and $R_{12}$ is an alkyl group, or a phenyl group which may have a substituent only at the m-position and/or p-position, is particularly suitable for use as a ligand component together with the Group VIII metal compound for the hydroformylation reaction of an olefinic compound. The hydrocarbon groups at the 3-, 6- and 8-positions of the 2-naphthyl group for $R_{10}$ and $R_{11}$, are preferably substituents of the following formula (V):

$$-CR_{16}R_{17}R_{18} \qquad (V)$$

wherein each or $R_{16}$, $R_{17}$ and $R_{18}$ is a hydrogen atom or a hydrocarbon group, preferably a $C_{1-10}$ hydrocarbon group. Among them, a $C_{3-20}$ branched alkyl group is most preferred.

The 4-, 5- and 7-positions of each of $R_{10}$ and $R_{11}$ are preferably substituted by the same substituents as those represented by $R_5$, $R_6$, $R_7$, $R_8$ and $R_9$ in the above formula (II).

Further, with respect to $R_{12}$, the preferred alkyl group, or the preferred phenyl group or substituted phenyl group, is the same as the alkyl group, or the phenyl group or substituted phenyl group for $R_3$ in the above formula (I).

Specific examples of the novel phosphite compound include bis(3,6,8-tri-i-propyl-2-naphthyl)(t-butyl)phosphite, bis(3,6,8-tri-i-propyl-2-naphthyl)cyclohexylphosphite, bis(3,6,8-tri-i-propyl-2-naphthyl)phenylphosphite, bis(3,6,8-tri-i-propyl-2-naphthyl)-p-cresylphosphite, bis(3,6,8-yti-i-propyl-2-naphthyl)(4-biphenyl)phosphite, bis(3,6,8-tri-i-propyl-2 -naphthyl)(4-acetylphenyl)phosphite, bis(3,6,8-tri-i-propyl-2-propyl-2-naphthyl)(4-benzoylphenyl)phosphite, bis(3,6,8-tri-i-propyl-2-naphthyl)(4-toluylphenyl)phosphite, bis(3,6,8-tri-i-propyl-2-naphthyl)(4-methanesulfonylphenyl)phosphite, bis(3,6,8-tri-i-propyl-2-naphthyl)(4-benzenesulfonylphenyl)phosphite, bis(3,6,8-tri-i-propyl-2 naphthyl)(4-toluenesulfonylphenyl)phosphite, bis(3,6,8-tri-sec-butyl-2-naphthyl)(t-butyl)phosphite, bis(3,6,8-tri sec-butyl-2-naphthyl)cyclohexylphosphite, bis(3,6,8-tri-sec-butyl-2-naphthyl)phenylphosphite, bis(3,6,8-tri-sec-butyl-2-naphthyl)-p-cresylphosphite, bis(3,6,8 tri-sec-butyl-2-naphthyl)(4-biphenyl)phosphite, bis(3,6,8-tri-sec-butyl-2-naphthyl)(4-acetylphenyl)phosphite, bis(3,6,8-tri-sec-butyl-2-naphthyl)(4-benzoylphenyl)phosphite, bis(3,6,8-tri-sec-butyl-2 naphthyl)(4-toluylphenyl)phosphite, bis(3,6,8-tri-sec-butyl-2-naphthyl)(4-methanesulfonylphenyl)phosphite, bis(3,6,8-tri-sec-butyl-2-naphthyl)(4-benzenesulfonylphenyl)phosphite, bis(3,6,8-tri-sec-butyl-2-naphthyl)(4-toluenesulfonylphenyl)phosphite, bis(3,6,8-tri-t-butyl-2-naphthyl)(t-butyl)phosphite, bis(3,6,8-tri-t-butyl-2-naphthyl)cyclohexylphosphite, bis(3,6,8-tri-t-butyl-2-naphthyl)phenylphosphite, bis(3,6,8-tri-t-butyl-2-naphthyl)-p-cresylphosphite, bis(3,6,8-tri-t-butyl-2-naphthyl)(4-biphenyl)phosphite, bis(3,6,8 tri-t-butyl-2-naphthyl)(4-acetylphenyl)phosphite, bis(3,6,8-tri-t-butyl- 2-naphthyl)(4-benzoylphenyl)phosphite, bis(3,6,8-tri-t-butyl-2-naphthyl)(4-toluylphenyl)phosphite, bis(3,6,8-tri-t-butyl-2-naphthyl)(4-methanesulfonylphenyl)phosphite, bis(3,6,8-tri-t-butyl-2-naphthyl)(4-benzenesulfonylphenyl)phosphite, bis(3,6,8-tri-t-butyl-2-naphthyl)(4-toluenesulfonylphenyl)phosphite, bis[3,6,8-tri(sec-n-amyl)-2naphthyl](t-butyl)phosphite, bis[3,6,8-tri(sec-n-amyl)-2-naphthyl]cyclohexylphosphite, bis[3,6,8-tri(sec-n-amyl)-2-naphthyl]phenylphosphite, bis[3,6,8-tri(sec-n-amyl)-2-naphthyl]-p-cresylphosphite, bis[3,6,8-tri(sec-n-amyl)-2-naphthyl](4-biphenyl)phosphite, bis[3,6,8-tri(-sec-n-amyl)-2-naphthyl](4 acetylphenyl)phosphite, bis[3,6,8-tri(sec n amyl)-2-naphthyl](4-benzoylphenyl)phosphite, bis[3,6,8-tri(sec-amyl)-2-naphthyl](4-toluylphenyl)phosphite, bis[3,6,8-tri(sec-n-amyl)-2-naphthyl](4-methanesulfonylphenyl)phosphite, bis[3,6,8-tri(-sec-n-amyl)-2-naphthyl](4-benzenesulfonylphenyl)phosphite, bis[3,6,8-tri(sec-n-amyl)-2-naphthyl](4-toluenesulfonylphenyl)phosphite, bis(3,6,8-tri-t-amyl 2-naphthyl)(t-butyl)phosphite, bis(3,6,8-tri-t-amyl-2 naphthyl)cyclohexylphosphite, bis(3,6,8-tri-t-amyl-2-naphthyl)phenylphosphite, bis(3,6,8-tri-t-amyl-2-naphthyl)-p-cresylphosphite, bis(3,6,8-tri-t-amyl-2-naphthyl)(4-biphenyl)phosphite, bis(3,6,8-tri-t-amyl-2-naphthyl)(4-acetylphenyl)phosphite, bis(3,6,8-tri-t-amyl-2 -naphthyl)(4-benzoylphenyl)phosphite, bis(3,6,8-tri-t-amyl-2-naphthyl)(4-toluylphenyl)phosphite, bis(3,6,8-tri-t-amyl-2-naphthyl)(4-methanesulfonylphenyl)phosphite, bis(3,6,8-tri-t-amyl-2-naphthyl)(4-benzenesulfonylphenyl)phosphite, bis(3,6,8-tri-t-amyl-2-naphthyl)(4-toluenesulfonylphenyl)phosphite, bis[3,6,8-tri(1,1,2-trimethylpropyl)-2-naphthyl](t-butyl)phosphite, bis[3,6,8-tri(1,1,2-trimethylpropyl)-2-naphthyl]cyclohexylphosphite, bis[3,6,8-tri(1,1,2-trimethylpropyl)-2-naphthyl]phenylphosphite, bis[3,6,8-tri(1,1,2-trimethylpropyl)-2-naphthyl]-p-cresylphosphite, bis[3,6,8-tri(1,1,2-trimethylpropyl)-2-naphthyl](4-biphenyl)phosphite, bis[3,6,8-tri(1,1,2-trimethylpropyl)-2-naphthyl](4-acetylphenyl)phosphite, bis[3,6,8-tri(1,1,2-trimethylpropyl) 2-naphthyl](4-benzoylphenyl)phosphite, bis[3,6,8-tri(1,1,2-trimethylpropyl)-2-naphthyl](4-toluylphenyl)phosphite, bis[3,6,8-tri(1,1,2 trimethylpropyl)-2-naphthyl](4-methanesulfonylphenyl)phosphite, bis[3,6,8-tri(1,1,2-trimethylpropyl)-2 naphthyl](4-benzenesulfonylphenyl)phosphite, and bis[3,6,8-tri(1,1,2-trimethylpropyl)-2-naphthyl](4-toluenesulfonylphenyl)phosphite.

A method for preparing a phosphite compound of the formula (III) of the present invention will be described. For example, phosphorus trichloride is reacted with naphthol compounds of the formulas $R_{10}OH$ and $R_{11}OH$ wherein $R_{10}$ and $R_{11}$ are as defined in the formula (III) in a solvent such as toluene in the presence of a hydrogen chloride receptor such as an amine, to obtain a corresponding monochloro intermediate of the formula $(R_{10}O)(R_{11}O)PCl$, which is then reacted with an alcohol compound or a phenol compound of the formula $R_{12}OH$ wherein $R_{12}$ is as defined in the formula (III) in the presence of a hydrogen chloride receptor such as an amine, whereby a corresponding phosphite compound can readily be produced.

The novel phosphite compound of the present invention has a feature that it has bulky hydrocarbon groups at the 3-, 6- and 8-positions of each of the two 2-naphthyl groups, which is bonded to phosphorus via an oxygen atom, and another group bonded to phosphorus via an oxygen atom is an alkyl group or a phenyl group having no substituent at the o-position. Such a specific structure presents high stability as a ligand and thus is essentially important for the improvement of the reaction rate thereby brought about.

Further, with the organic phosphite ligand of the present invention, no substantial decrease in the activities is observed by an increase of the amount, and it is useful within a wide range of concentration, which is preferred also from the viewpoint of the process management. Accordingly, the amount of the organic phosphite ligand of the present invention is suitably determined from the economical aspect. However, it is usually selected within a range of from 1 to 500 mol times, preferably from 1 to 100 mol times, more preferably from 5 to 50 mol times, relative to the Group VIII metal which will be described hereinafter.

The Group VIII metal compound to be used in the present invention is a compound of a metal selected from Group VIII transition metals such as rhodium, cobalt, platinum, iridium, palladium, ruthenium and a mixture thereof. Preferred types of the metal are rhodium, cobalt and platinum. Particularly preferred is rhodium. The form in which the Group VIII metal compound is incorporated, is not particularly limited. For example, rhodium may be incorporated in the form of rhodium metal supported on a carrier such as alumina, silica or active carbon, an inorganic or organic salt of rhodium, such as rhodium chloride, rhodium nitrate, rhodium acetate, rhodium formate, sodium rhodium chloride or potassium rhodium chloride, a chelating compound of rhodium such as rhodium dicarbonyl acetyl acetonate, or a carbonyl complex compound of rhodium such as tetrarhodium dodecacarbonyl, hexarhodium hexadecacarbonyl, $\mu,\mu'$-dichlororhodium tetracarbonyl, [Rh(OAc)(COD)]$_2$ or [Rh($\mu$-S-t-Bu)(CO)$_2$]$_2$, wherein COD represents 1,5-cyclooctadiene. Other Group VIII transition metal compounds include, for example, a cobalt compound such as dicobalt octacarbonyl or cobalt stearate, a platinum compound such as platinic acid, sodium hexachloroplatinate or potassium platinate, an iridium compound such as iridium trichloride or iridium carbonyl, a palladium compound such as palladium acetate or palladium chloride, and a ruthenium compound such as ruthenium trichloride or tetraamine hydroxychlororuthenium chloride. The amount of the Group VIII metal compound is not particularly limited, and the lower and upper limits are usually determined from the viewpoint of the catalytic activities and the economical feasibility. It is usually selected within a range of from 0.05 mg to 5 g, preferably from 0.5 mg to 1 g, more preferably from 1 to 300 mg, per liter of the olefinic compound, as calculated as the metal atom in the hydroformylation reaction zone.

The Group VIII metal compound forms a carbonyl complex active for the hydroformylation reaction in the reaction system.

For the hydroformylation reaction, a solvent is not necessarily required. However, if necessary, a solvent inert to the hydroformylation reaction may be employed. A preferred solvent may, for example, be a saturated hydrocarbon compound such as hexane, octane, decane, tetradecane or hexadecane, an aromatic hydrocarbon compound such as toluene, xylene or dodecylbenzene, a ketone such as acetone, diethyl ketone or methyl ethyl ketone, an ether such as tetrahydrofuran or dioxane, or an ester such as ethyl acetate or di-n-octyl phthalate.

In the present invention, the reaction conditions for the hydroformylation reaction are similar to those commonly employed in the conventional hydroformylation reaction. Namely, the reaction temperature is selected within a range of from 20° to 200° C., preferably from 50° to 150° C. The reaction pressure is selected usually within a range of from atmospheric pressure to 200 atm, preferably from 5 to 100 atm, more preferably from 10 to 80 atm. The molar ratio of hydrogen to carbon monoxide (H$_2$/CO) is selected usually within a range of from 10/1 to 1/10, preferably from 4/1 to 1/4.

The hydroformylation reaction may be conducted in a continuous system, a semi-batch system or a batch system in an agitation-type reactor or a bubble tower type reactor. Further, separation of the formed aldehyde and the catalyst solution can be conducted by a known method such as distillation. This distillation method may be conducted in a continuous system or in a batch system. It may be conducted under an elevated pressure, atmospheric pressure or reduced pressure. The temperature is suitably selected within a range of from 20° to 200° C., preferably from 50° to 170° C., as the case requires. The catalyst solution separated by distillation may be recycled in its entire amount or a part thereof to the hydroformylation step in conventional manner for reuse.

In the present invention, it is the main object to obtain from a starting material olefin a corresponding aldehyde. However, in the hydroformylation step, a corresponding alcohol also forms usually in an amount of a few %.

Now, the method of the present invention will be described in further detail with reference to Examples. However, it should be understood that present invention is by no means restricted by such specific Examples.

EXAMPLE 1

Into a stainless steel autoclave of magnetic stirring type having an internal capacity of 200 ml, 90 ml of an octene isomer mixture obtained by dimerization of butene, 10 ml of m-xylene, 25 mg (0.098 mmol) of rhodium carbonyl acetyl acetonate and 780 mg (0.98 mmol) of tris(3,6-di-t-butyl-2-naphthyl)phosphite were charged under a nitrogen atmosphere. Then, the interior of the autoclave was flushed with nitrogen. The autoclave was heated to 130° C. under stirring. After the temperature reached 130° C., a 1:1 gas mixture of hydrogen and carbon monoxide was injected to a level of 50 kg/cm$^2$G from a pressure container having an internal capacity of 200 ml via a constant pressure reactor, and the internal pressure of the autoclave was maintained at a level of 50 kg/cm$^2$G. After the reaction for 5 hours, the autoclave was cooled and purged to atmospheric pressure, and the content was taken out under a nitrogen atmosphere. The content was analyzed by gas chromatography, whereby the conversion of the starting material octene was found to be 94.4% (yield of C$_9$ aldehyde: 90.1%, yield of C$_9$ alcohol: 3.8%).

EXAMPLES 2 and 3

The operation was conducted in the same manner as in Example 1 except that the rhodium concentration and the P/Rh ratio were changed. The results are shown in Table 1 together with the results in Example 1.

TABLE 1

| Example No. | P/Rh ratio (molar ratio) | Conversion of octene (%) | Yield of C$_9$ aldehyde (%) | Yield of C$_9$ alcohol (%) |
|---|---|---|---|---|
| 1 | 10 | 94.4 | 90.1 | 3.8 |
| 2 | 30 | 93.2 | 90.5 | 1.8 |
| 3 | 3 | 92.2 | 87.7 | 3.5 |

EXAMPLE 4

In Example 1, after the reaction for 5 hours, the autoclave was cooled and purged to atmospheric pressure, and the content was taken out under a nitrogen atmosphere. The content was analyzed by gas chromatography, whereby the conversion of starting material octene was found to be 92.8%. This content was distilled under reduced pressure to separate the formed aldehyde. To the distillation residue thereby obtained, 90 ml of the octene isomer mixture as used in Example 1 and 10 ml of m-xylene were added. The mixture was reacted at 130° C. for 5 hours under a pressure of 50 kg/cm$^2$G in the same manner as in the first reaction. The autoclave was cooled and purged, and then the content was analyzed by gas chromatography, whereby the conversion of starting material octene was found to be 92.7%. Thus, no deterioration in the activity was found in the recycled use as compared with the first reaction.

EXAMPLE 5

The reaction was conducted in the same manner as in Example 1 except that 861 mg (0.98 mmol) of tris(3,6-di-t-amyl-2 naphthyl)phosphite was used instead of tris(3,6-di-t-butyl-2-naphthyl)phosphite. As a result, the conversion of starting material octene was 92.3% (yield of $C_9$ aldehyde: 88.7%, yield of $C_9$ alcohol: 3.0%).

COMPARATIVE EXAMPLE 1

The reaction was conducted in the same manner as in Example 1 except that 633 mg (0.98 mmol) of tris(2,4-di-t-butylphenyl)phosphite was used instead of tris(3,6-di-t-butyl-2-naphthyl)phosphite. As a result, the conversion of starting material octene was 90.8% (yield of $C_9$ aldehyde: 87.4%, yield of $C_9$ alcohol: 2.9%).

COMPARATIVE EXAMPLE 2

The reaction was conducted in the same manner as in Example 1 except that 274 mg (0.98 mmol) of tricyclohexylphosphine was used instead of tris(3,6-di-t-butyl-2-naphthyl)phosphite. As a result, the conversion of starting material octene was 46.4% (yield of $C_9$ aldehyde: 46.3%, yield of $C_9$ alcohol: 0%).

EXAMPLE 6

Into a stainless steel autoclave of magnetic stirring type having an internal capacity of 200 ml, 30 ml of 2-methyl-2-butene, 45 ml of m-xylene, 5 ml of n-tetradecane, 10 mg (0.039 mmol) of rhodium dicarbonyl acetyl acetonate, and 310 mg (0.39 mmol) of tris(3,6-di-t-butyl-2-naphthyl)phosphite were charged under a nitrogen atmosphere. Then, the interior of the autoclave was flushed with nitrogen. The autoclave was heated to 130° C. under stirring. After the temperature reached 130° C., a 1:1 gas mixture of hydrogen and carbon monoxide was injected to a level of 50 kg/cm²G from a pressure container having an internal capacity of 200 ml via a constant pressure reactor, and the internal pressure of the autoclave was maintained at a level of 50 kg/cm²G. After the reaction for one hour, the autoclave was cooled and purged to atmospheric pressure, and the content was taken out under a nitrogen atmosphere. The content was analyzed by gas chromatography, whereby the conversion of the starting material 2-methyl-2-butene was found to be 8.1%.

COMPARATIVE EXAMPLE 3

The reaction was conducted in the same manner as in Example 3 except that 252 mg (0.39 mmol) of tris(2,4-di-t-butylphenyl)phosphite was used instead of tris(3,6-di-t-butyl-2-naphthyl)phosphite. As a result, the conversion of starting material 2-methyl-2-butene was 74.2%.

EXAMPLE 7

Into a 200 ml four-necked flask equipped with a stirrer and a reflux condenser, 1.57 g (0.011 mol) of phosphorus trichloride and 20 ml of toluene were charged and stirred under a nitrogen atmosphere. A uniform mixture comprising 7.16 g (0.023 mol) of 3,6,8-tri-t-butyl-β-naphthol, 2.55 g (0.25 mol) of triethylamine and 30 ml of toluene, was dropwise added to the above flask over a period of one hour at room temperature under stirring. After the dropwise addition, stirring was continued at room temperature for 4 hours. Then, a uniform mixture comprising 1.15 g (0.011 mol) of cyclohexanol, 1.27 g (0.012 mol) of triethylamine and 20 ml of toluene, was further dropwise added over a period of 30 minutes at room temperature. Then, the flask was heated in an oil bath, and the mixture was refluxed for 3 hours to complete the reaction. Then, solid of triethylamine hydrochloride produced as a byproduct by the reaction, was removed by filtration. Then, toluene as the solvent was distilled off under reduced pressure. To the residue, 200 ml of acetonitrile was added to let white solid precipitate. The precipitated solid was collected by filtration, dried and suspension-washed at room temperature in 200 ml of acetonitrile. Then, it was collected by filtration, and dried to obtain 8.0 g of bis(3,6,8-tri-t-butyl-2-naphthyl)cyclohexylphosphite (yield relative to charged phosphorus trichloride: 93%).

EXAMPLES 8 to 11

The operation was conducted in the same manner as in Example 7 except that instead of cyclohexanol, phenol, p-phenylphenol, 4-hydroxyphenylsulfone, or 4-hydroxybenzophenone, was used, whereby bis(3,6,8-tri t-butyl-2-naphthyl)phenylphosphite, bis(3,6,8-tri-t butyl-2-naphthyl)(4-biphenyl)phosphite, bis(3,6,8-tri-t-butyl-2-naphthyl)(4-benzenesulfonylphenyl)phosphite or bis(3,6,8-tri-t-butyl-2-naphthyl)(4-benzoylphenyl)-phosphite was obtained in the yield of 95%, 39%, 81% or 92%, respectively (yield relative to charged phosphorus trichloride).

The structures of the above phosphite compounds were ascertained by a ¹H NMR method (JEOL JNM-GX270, a ³¹PNMR method (JEOL JNM -FX100), an elemental analysis and a SIMS mass analysis (Hitachi M-200A). The analytical values are shown in Tables 2 and 3.

TABLE 2

| Example No. | Phosphite compound*2 | ³¹p nmr*¹ Chemical shift (ppm) | Elemental analysis | | | | SIMS molecular ion mass |
| --- | --- | --- | --- | --- | --- | --- | --- |
| | | | | C | H | P | S |
| 7 | [structure] | 128.04 | Calculated | 79.74 | 9.77 | 4.11 | | — |
| | | | Found | 79.71 | 9.97 | 4.55 | | |

TABLE 2-continued

| Example No. | Phosphite compound*2 | $^{31}$p nmr*1 Chemical shift (ppm) | Elemental analysis | | | | | SIMS molecular ion mass |
|---|---|---|---|---|---|---|---|---|
| | | | | C | H | P | S | |
| 8 | (naphthalene with t-Bu and cyclohexyl substituents)₂–O–P–O–phenyl | 127.58 | Calculated | 80.39 | 9.04 | 4.15 | | 746[M+] |
| | | | Found | 80.42 | 9.41 | 4.11 | | |
| 9 | (naphthalene with t-Bu and cyclohexyl substituents)₂–O–P–O–biphenyl | 127.40 | Calculated | 81.71 | 8.69 | 3.76 | | 822[M+] |
| | | | Found | 81.13 | 9.16 | 3.71 | | |
| 10 | (naphthalene with t-Bu and cyclohexyl substituents)₂–O–P–O–phenyl–SO₂–phenyl | 126.94 | Calculated | 75.81 | 8.07 | 3.49 | 3.61 | 866[M+] |
| | | | Found | 75.65 | 8.20 | 3.41 | 3.38 | |
| 11 | (naphthalene with t-Bu and cyclohexyl substituents)₂–O–P–O–phenyl–C(=O)–phenyl | 127.03 | Calculated | 80.43 | 8.41 | 3.64 | | 850[M+] |
| | | | Found | 80.62 | 8.56 | 3.41 | | |

[1] $^{31}$p nmr is the value relative to H₃PO₄ standard (0 ppm).

[2] + represents a t-butyl group and ⟨H⟩ represents a cyclohexyl group.

TABLE 3

| Example No. | Phosphite compound*2 | $^1$H nmr*1 Chemical shift (ppm) (integrated value) |
|---|---|---|
| 8 | (naphthalene with t-Bu and cyclohexyl substituents)₂–O–P–O–phenyl | t-Butyl: 1.40[18H] 1.48[18H] 1.53[18H]<br>Naph-ring*3: 7.53[2H] 7.59[2H] 7.79[2H] 8.51[2H]<br>Ar-ring*3: 7.0–7.3[5H] |
| 9 | (naphthalene with t-Bu and cyclohexyl substituents)₂–O–P–O–biphenyl | t-Butyl: 1.40[18H] 1.48[18H] 1.53[18H]<br>Naph-ring: 7.53[2H] 7.59[2H] 7.79[2H] 8.51[2H]<br>Ar-ring: 7.1–7.8[9H] |

TABLE 3-continued

| Example No. | Phosphite compound*2 | $^1$H nmr*[1] Chemical shift (ppm) (integrated value) | |
|---|---|---|---|
| 10 | (structure: bis(di-t-butyl-naphthyl) (phenylsulfonylphenyl) phosphite) | t-Butyl:<br>Naph-ring<br>Ar-ring | 1.41[36H] 1.48[18H]<br>7.52[2H] 7.58[2H] 7.77[2H] 8.41[2H]<br>7.1–7.9[9H] |
| 11 | (structure: bis(di-t-butyl-naphthyl) (benzoylphenyl) phosphite) | t-Butyl:<br>Naph-ring<br>Ar-ring | 1.40[18H] 1.49[18H] 1.53[18H]<br>7.51[2H] 7.60[2H] 7.80[2H] 8.49[2H]<br>7.1–7.8[9H] |

*[1]$^1$H nmr is the value relative to $(CH_3)_4Si$ standard (0 ppm).
*[2] + represents a t-butyl group.
*[3] Naph-ring represents a naphthalene ring, and Ar-ring represents an aromatic ring other than a naphthalene ring.

EXAMPLE 12

Into a stainless steel autoclave of magnetic stirring type having an internal capacity of 200 ml, 90 ml of an octene mixture obtained by dimerization of butene, 10 ml of m-xylene, 25 mg (0.098 mmol) of rhodium dicarbonylacetyl acetonate and 806 mg (0.98 mmol) of bis(3,6,8-tritert-butyl 2 naphthyl)(4-biphenyl)phosphite were charged under a nitrogen atmosphere. Then, the interior of the autoclave was flushed with nitrogen. The autoclave was heated to 130° C. under stirring. After the temperature reached 130° C., a 1:1 gas mixture of hydrogen and carbon monoxide was injected to a pressure of 50 kg/cm$^2$G from a pressure container having an internal capacity of 200 ml via a constant pressure reactor, and the internal pressure of the autoclave was maintained at a level of 50 kg/cm$^2$G. After the reaction for 5 hours, the autoclave was cooled and purged to atmospheric pressure, and the content was taken out under a nitrogen atmosphere. The content was analyzed by gas chromatography, whereby the conversion of starting material octene was found to be 91.4% (yield of aldehyde: 7.3%, yield of alcohol: 4.1%).

EXAMPLE 13

The reaction was conducted in the same manner as in Example 12 except that 730 mg (0.98 mmol) of bis(3,6,8-tritert-butyl-2-naphthyl)phenylphosphite was used as the organic phosphite compound. As a result, the conversion of starting material octene was 90.8% (yield of aldehyde: 87.1%, yield of alcohol: 3.9%).

EXAMPLE 14

The reaction was conducted in the same manner as in Example 12 except that 735 mg (0.98 mmol) of bis(3,6,8-tritert-butyl-2-naphthyl)cyclohexylphosphite was used as the organic phosphite compound. As a result, the conversion of starting material octene was 84.5% (yield of aldehyde: 82.6%, yield of alcohol: 1.9%).

EXAMPLE 15

After the reaction for 5 hours in the same manner as in Example 12, the autoclave was cooled and purged to atmospheric pressure, and the content was taken out under a nitrogen atmosphere. Then, the content was distilled under reduced pressure to separate the formed aldehyde. To the distillation residue thereby obtained, 90 ml of the octene mixture and 10 ml of m xylene were added, and the mixture was reacted at 130° C. for 5 hours under a pressure of 50 kg/cm$^2$G in the same manner as in the first reaction. The autoclave was cooled and purged, and the content was analyzed by gas chromatography, whereby the conversion of starting material octene was found to be 91.1% (yield of aldehyde: 85.8%, yield of alcohol: 5.3%). Thus, no deterioration in the catalytic activities was observed in the recycled use of the catalyst as compared with the first reaction.

EXAMPLE 16

The reaction was conducted in the same manner as in Example 12 except that 7.5 mg (0.029 mmol) of rhodium dicarbonyl acetyl acetonate and 241 mg (0.29 mmol) of bis(3,6,8-tritert-butyl-2-naphthyl)(4-biphenyl)phosphite were used. As a result, the conversion of starting material octene was 86.1% (yield of aldehyde: 83.4%, yield of alcohol: 2.7%).

EXAMPLES 17 to 19

The reaction was conducted in the same manner as in Example 16 except that instead of bis(3,6,8-tritert-butyl-2-naphthyl)(4-biphenyl)phosphite, 218 mg (0.29 mmol) of bis(3,6,8-tritert-butyl-2-naphthyl)phenylphosphite, 250 mg (0.29 mmol) of bis (3,6,8-tritert-butyl-2-naphthyl)(4-benzoylphenyl)phosphite, or 259 mg (0.29 mmol) of bis(3,6,8-tritert-butyl-2-naphthyl)(4-benzenesulfonylphenyl)phosphite, was used. The results are shown in Table 4 together with the results of Example 16.

TABLE 4

| Example No. | Phosphite compound | Conversion of octene (%) | Yield of aldehyde (%) | Yield of alcohol (%) |
|---|---|---|---|---|
| 16 | | 86.1 | 83.4 | 2.7 |
| 17 | | 84.9 | 82.8 | 2.1 |
| 18 | | 85.7 | 82.7 | 3.0 |
| 19 | | 83.2 | 80.7 | 2.5 |

EXAMPLE 20

Into a stainless steel autoclave of magnetic stirring type having an internal capacity of 200 ml, 30 ml of 2-methyl-2-butene, 45 ml of m-xylene, 5 ml of n-tetradecane, 10 mg (0.039 mmol) of rhodium dicarbonyl acetyl acetonate and 319 mg (0.39 mmol) of bis(3,6,8-tritert-butyl-2-naphthyl)(4-biphenyl)phosphite were charged under a nitrogen atmosphere. Then, the interior of the autoclave was flushed with nitrogen. The autoclave was heated to 130° C. under stirring. After the temperature reached 130° C., a 1:1 gas mixture of hydrogen and carbon monoxide was charged to a pressure of 50 kg/cm²G from a pressure container having an internal capacity of 200 ml via a constant pressure reactor, and the internal pressure of the autoclave was maintained at a level of 50 kg/cm²G. After the reaction for one hour, the autoclave was cooled and purged to atmospheric pressure, and the content was taken out under a nitrogen atmosphere. The content was analyzed by gas chromatography, whereby the conversion of starting material 2 methyl-2-butene was found to be 78.2%.

EXAMPLE 21

The reaction was conducted in the same manner as in Example 20 except that 291 mg (0.39 mmol) of bis(3,6,8-tritert-butyl-2-naphthyl)phenylphosphite was used as the organic phosphite compound. As a result, the conversion of starting material 2-methyl-2-butene was 80.7%.

What is claimed is:
1. A phosphite compound of formula (III):

$$P(OR_{10})(OR_{11})(OR_{12}) \quad \text{(III)}$$

wherein each of $R_{10}$ and $R_{11}$ is a 2-naphthyl group in which at least the 3-, 6- and 8-positions are substituted by the same or different hydrocarbon groups of formula (V):

$$-CR_{16}R_{17}R_{18} \quad \text{(V)}$$

wherein each of $R_{16}$, $R_{17}$ and $R_{18}$ is a hydrogen atom or a hydrocarbon group, and $R_{12}$ is an alkyl group or a phenyl group of the formula:

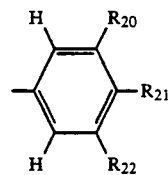

wherein each of $R_{20}$, $R_{21}$ and $R_{22}$ is a hydrogen atom or an optional organic group.

2. The phosphite compound according to claim 1, wherein each of $R_{16}$, $R_{17}$ and $R_{18}$ is a $C_{1-10}$ hydrocarbon group.

3. The phosphite compound according to claim 1, wherein said hydrocarbon groups are $C_{3-20}$ branched alkyl groups.

4. The phosphite compound according to claim 1, wherein said optional organic group is a member selected from the group consisting of a $C_{1-30}$ hydrocarbon group, a halogen atom, a fluorinated alkyl group, an alkoxy group, an acyl group, a carboalkoxy group, furyl, pyranyl, amino, an alkylamino group, an aminoalkyl group, cyano, a cyanoalkyl group, nitro, an alkylsulfonyl group and an aryl sulfonyl group.

5. The phosphite compound according to claim 1, wherein said optional organic group is a member selected from the group consisting of a $C_{1-30}$ alkyl group, a $C_{6-30}$ aryl group, a $C_{7-30}$ aralkyl group, halogen, a $C_{1-10}$ fluorinated alkyl group, a $C_{1-10}$ alkoxy group, a $C_{1-20}$ acyl group, a $C_{1-20}$ carboalkoxy group, furyl, pyranyl, amino, a $C_{1-20}$ alkylamino group, a $C_{1-10}$ aminoalkyl group, cyano, a $C_{1-10}$ cyanoalkyl group, nitro, a $C_{6-10}$ alkylsulfonyl group and a $C_{1-20}$ arylsulfonyl group.

6. The phosphite compound according to claim 1, wherein said optional organic group is a member selected from the group consisting of a $C_{1-30}$ alkyl group, a $C_{6-30}$ aryl group, a $C_{7-30}$ aralkyl group, halogen, a $C_{1-5}$ fluorinated alkyl group, a $C_{1-5}$ alkoxy group, a $C_{1-5}$ acyl group, a $C_{1-5}$ carboalkoxy group, furyl, pyranyl, amino, a $C_{1-5}$ alkylamino group, a $C_{1-5}$ amino alkyl group, cyano, a $C_{1-5}$ cyanoalkyl group, nitro, a $C_{1-5}$ alkylsulfonyl group and a $C_{6-10}$ arylsulfonyl group.

7. The phosphite compound according to claim 1, wherein $R_{12}$ is a $C_{1-20}$ alkyl group.

8. The phosphite compound according to claim 1, wherein $R_{12}$ is a branched or cyclic alkyl group.

9. The phosphite compound according to claim 1, wherein the substituents at the 4-, 5- and 7-positions of the 2-naphthyl group for each of $R_{10}$ and $R_{11}$ are the same or different and are selected from the group consisting of hydrogen and an organic group.

10. The phosphite compound according to claim 9, wherein the organic group is a member selected from the group consisting of a $C_{1-20}$ alkyl group, a $C_{6-30}$ aryl group, a $C_{7-30}$ aralkyl group, halogen, alkoxy, carboalkoxy, an alkylamino group and a fluorinated alkyl group.

* * * * *